US007145044B2

(12) United States Patent
Ueda et al.

(10) Patent No.: US 7,145,044 B2
(45) Date of Patent: Dec. 5, 2006

(54) METHOD OF PRODUCING REDUCED COENZYME $Q_{10}$ USING SOLVENT WITH HIGH OXIDATION-PROTECTIVE EFFECT

(75) Inventors: Takahiro Ueda, Hyogo (JP); Shiro Kitamura, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 59 days.

(21) Appl. No.: 10/483,604

(22) PCT Filed: Jul. 15, 2002

(86) PCT No.: PCT/JP02/07143

§ 371 (c)(1), (2), (4) Date: Jun. 1, 2004

(87) PCT Pub. No.: WO03/006408

PCT Pub. Date: Jan. 23, 2003

(65) Prior Publication Data

US 2004/0215040 A1 Oct. 28, 2004

(30) Foreign Application Priority Data

Jul. 13, 2001 (JP) ............................ 2001-214471
Apr. 17, 2002 (JP) ............................ 2002-114854

(51) Int. Cl.
*C07C 35/18* (2006.01)
*C07C 50/04* (2006.01)
*C12N 15/00* (2006.01)

(52) U.S. Cl. ...................... 568/823; 568/830; 552/293; 435/816

(58) Field of Classification Search ................ 568/823, 568/830; 552/293; 435/816
See application file for complete search history.

(56) References Cited

U.S. PATENT DOCUMENTS 6,184,255 B1 2/2001 Mae et al. .................. 514/720

FOREIGN PATENT DOCUMENTS

| | | | |
|---|---|---|---|
| EP | 0 956 854 | A1 | 11/1999 |
| GB | 947643 | | 1/1964 |
| JP | 52-72884 | | 6/1977 |
| JP | 52-072884 | A2 | 6/1977 |
| JP | 53-133687 | | 11/1978 |
| JP | 53-133687 | A2 | 11/1978 |
| JP | 54-140793 | A2 | 11/1979 |
| JP | 56-92238 | | 7/1981 |
| JP | 56-092238 | A2 | 7/1981 |
| JP | 57-70834 | | 5/1982 |
| JP | 57-070834 | A2 | 5/1982 |
| JP | 60-75294 | | 4/1985 |
| WO | WO 96/17626 | | 6/1996 |
| WO | WO 98/04512 | A | 2/1998 |

OTHER PUBLICATIONS

International Search Report From Corresponding International Application No. PCT/JP02/07143, Dated Oct. 21, 2002, 1 Page.

Patent Cooperation Treaty International Preliminary Examination Report (PCT Article 36 and Rule 70), From Corresponding International Application No. PCT/JP02/07143, Dated Aug. 19, 2003, 4 Pages.

Foti, M. et al., "The Surprisingly High Reactivity of Phenoxyl Radicals," *J. Am. Chem. Soc.*, vol. 116, No. 21, 1994, pp. 9440-9447.

Supplementary European Search Report from Application No. EP 02 74 6036, Dated Mar. 10, 2005, 5 pages.

*Primary Examiner*—Sikarl A. Witherspoon
(74) *Attorney, Agent, or Firm*—Brinks Hofer Gilson & Lione

(57) ABSTRACT

The present invention relates to a method of conveniently and efficiently producing reduced coenzyme $Q_{10}$ having excellent qualities which is useful in foods, functional nutritive foods, specific health foods, nutritional supplements, nutrients, drinks, feeds, animal drugs, cosmetics, medicines, remedies, preventive drugs, etc. This method is suitable for industrial production thereof.

In a method of synthesizing reduced coenzyme $Q_{10}$ by reducing oxidized coenzyme $Q_{10}$, followed by crystallization, at least one species selected from among hydrocarbons, fatty acid esters, ethers and nitrites is used as a solvent. Thus, the reduced coenzyme $Q_{10}$ can be protected from oxidation, and as a result, the formation of the oxidized coenzyme $Q_{10}$ as a by-product can be minimized, thereby giving reduced coenzyme $Q_{10}$ having excellent qualities.

31 Claims, No Drawings

METHOD OF PRODUCING REDUCED COENZYME $Q_{10}$ USING SOLVENT WITH HIGH OXIDATION-PROTECTIVE EFFECT

RELATED APPLICATIONS

This application is a nationalization of PCT Application No. PCT/JP02/07143 filed Jul. 15, 2002. This application claims priority from Japanese Patent Application No. 2001-214471 filed on Jul. 13, 2001 and Japanese Patent Application No. 2002-114854 filed on Apr. 17, 2002.

TECHNICAL FIELD

The present invention relates to a method of synthesizing and a method of crystallizing reduced coenzyme $Q_{10}$. Reduced coenzyme $Q_{10}$ shows a higher level of oral absorbability as compared with oxidized coenzyme $Q_{10}$ and is a compound useful as an ingredient in good foods, functional nutritive foods, specific health foods, nutritional supplements, nutrients, drinks, feeds, animal drugs, cosmetics, medicines, remedies, preventive drugs, etc.

BACKGROUND ART

Oxidized coenzyme $Q_{10}$, which is a benzoquinone derivative widely distributed in the biological world, is also called vitamin Q because of its vitamin-like function and is an ingredient acting as a nutrient in restoring the cell activity that has been weakened to its healthy condition and rejuvenating the body. On the other hand, reduced coenzyme $Q_{10}$, which is derived from oxidized coenzyme $Q_{10}$ by two-electron reduction, is as white crystals as compared with oxidized coenzyme $Q_{10}$ being as orange-colored crystals. Reduced coenzyme $Q_{10}$ and oxidized coenzyme $Q_{10}$ are known to be localized in the mitochondrion, lysosome, Golgi body, microsome, peroxisome, and cell membrane, among others, and involved, as constituents of the electron transport system, in ATP production and activation, in vivo antioxidant activity, and membrane stabilization; they are thus substances indispensable for body function maintenance.

It is known that reduced coenzyme $Q_{10}$ can be prepared by producing coenzyme $Q_{10}$ in the conventional manner, for example by synthesis, fermentation, or extraction from natural products, and concentrating a reduced coenzyme $Q_{10}$-containing eluate fraction resulting from chromatography (JP-A-10-109933). On that occasion, as described in the above-cited publication, the chromatographic concentration may be carried out after reduction of oxidized coenzyme $Q_{10}$ contained in the reduced coenzyme $Q_{10}$ with a conventional reducing agent such as sodium borohydride or sodium dithionite (sodium hyposulfite), or reduced coenzyme $Q_{10}$ may be prepared by reacting the reducing agent mentioned above with an existing highly pure grade of coenzyme $Q_{10}$ (oxidized form). However, the thus-obtained reduced coenzyme $Q_{10}$ cannot always be in a highly pure state but tends to occur as a low-purity crystalline, semisolid, or oily product containing such impurities as oxidized coenzyme $Q_{10}$.

JP-A-57-70834 discloses an example in which reduced coenzyme $Q_{10}$ was synthesized by dissolving coenzyme $Q_{10}$ in hexane and adding an aqueous solution of sodium hydrosulfite (sodium hyposulfite) to the solution, followed by stirring. However, sodium dithionite was used as a reducing agent in an amount as large as twice the weight of coenzyme $Q_{10}$. Thus, such method of synthesis has problems from the economical viewpoint as well as complexity viewpoint of the subsequent purification procedure.

Reduced coenzyme $Q_{10}$ is readily oxidized to oxidized coenzyme $Q_{10}$ by molecular oxygen. On a commercial production scale, complete oxygen elimination is very difficult to achieve and, furthermore, fairly long periods of time are required for individual operations, unlike laboratory scale production, so that residual oxygen exerts a great adverse effect. The oxidation in question is directly connected with such yield and quality problems as the formation of hardly eliminable oxidized coenzyme $Q_{10}$ and adulteration of the product therewith. For obtaining highly pure reduced coenzyme $Q_{10}$ in the form of crystals, it is important to adequately protect the reduced form from the oxidation mentioned above.

SUMMARY OF THE INVENTION

In view of the foregoing, the present invention has an object to provide a convenient and efficient method of synthesizing and of crystallizing high-quality reduced coenzyme $Q_{10}$. Furthermore, the present invention has another object to provide an outstanding method for obtaining high-quality reduced coenzyme $Q_{10}$ in the form of crystals which is suited for the production thereof on a commercial scale.

The present inventors made intensive investigations, and as a result, found that when placed in a specific solvent, reduced coenzyme $Q_{10}$ is favorably protected from oxidation by molecular oxygen and, based on this finding, they have completed the present invention.

Thus, the present invention provides a method of producing reduced coenzyme $Q_{10}$ which comprises using at least one species selected from among hydrocarbons exclusive of hexane, fatty acid esters, ethers and nitriles as a solvent in synthesizing reduced coenzyme $Q_{10}$ by reduction of oxidized coenzyme $Q_{10}$.

The invention also provides a method for producing reduced coenzyme $Q_{10}$ which comprises using a hydrocarbon as a solvent in a deoxygenated atmosphere in synthesizing reduced coenzyme $Q_{10}$ by reduction of oxidized coenzyme $Q_{10}$.

The invention further provides a method for crystallizing reduced coenzyme $Q_{10}$, which comprises crystallizing the reduced coenzyme $Q_{10}$ using, as a solvent, at least one species selected from the group consisting of hydrocarbons, fatty acid esters, ethers and nitrites.

The invention further provides a method for stabilizing reduced coenzyme $Q_{10}$ which comprises handling reduced coenzyme $Q_{10}$ in the form of a solution in at least one solvent selected from among hydrocarbons, fatty acid esters, ethers and nitriles to thereby protect the reduced coenzyme $Q_{10}$ from oxidation by molecular oxygen.

The invention still further provides a reduced coenzyme $Q_{10}$ crystal with a reduced coenzyme $Q_{10}$/oxidized coenzyme $Q_{10}$ weight ratio of not lower than 96/4.

In accordance with the present invention, it is possible, in synthesizing reduced coenzyme $Q_{10}$ by reduction of oxidized coenzyme $Q_{10}$, to favorably protect the reduced coenzyme $Q_{10}$ from oxidation by molecular oxygen and, thus, it is possible to synthesize high-quality reduced coenzyme $Q_{10}$ in such a condition that the formation of oxidized coenzyme $Q_{10}$ as a byproduct is minimized. Furthermore, the method of crystallizing reduced coenzyme $Q_{10}$ of the present invention makes it possible to favorably protect reduced coenzyme $Q_{10}$ from oxidation by molecular oxygen and, thus it is possible to convert the same into a crystalline state in such a condition that the formation of oxidized coenzyme $Q_{10}$ as a byproduct is minimized and thereby obtain high-quality crystalline coenzyme $Q_{10}$.

DETAILED DISCLOSURE OF THE INVENTION

In the following, the present invention is described in detail.

In accordance with the invention, a solvent highly effective in protecting reduced coenzyme $Q_{10}$ from the above-mentioned oxidation, namely at least one species selected from among hydrocarbons, fatty acid esters, ethers, and nitriles is used for synthesizing high-quality reduced coenzyme $Q_{10}$ and for crystallizing the same and, further, for handling reduced coenzyme $Q_{10}$ stably, while inhibiting the oxidation of reduced coenzyme $Q_{10}$ to oxidized coenzyme $Q_{10}$ by molecular oxygen. Surprisingly, reduced coenzyme $Q_{10}$ is adequately protected from oxidation by molecular oxygen in a state dissolved or suspended in the solvents mentioned above rather in a crystalline state. Such oxidation-protective effect of the solvents has been found for the first time by the present inventors.

The hydrocarbons are not particularly restricted, but there may be mentioned, for example, aliphatic hydrocarbons, aromatic hydrocarbons, halogenated hydrocarbons, etc. Preferred are aliphatic hydrocarbons and aromatic hydrocarbons, and more preferred are aliphatic hydrocarbons.

The aliphatic hydrocarbons are not particularly restricted, and may be cyclic or acyclic, or saturated or unsaturated. However, generally they contain 3 to 20 carbon atoms, and preferably 5 to 12 carbon atoms.

As specific examples, there may be mentioned, for example, propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, etc.

Among them, saturated aliphatic hydrocarbons having 5 to 8 carbon atoms are more preferred, and preferably used are pentane, 2-methylbutane and cyclopentane, which have 5 carbon atoms (referred to as "pentanes"); hexane, 2-methylpentane, 2,2-dimethylbutane, 2,3-dimethylbutane, methylcyclopentane, cyclohexane, which have 6 carbon atoms (referred to as "hexanes"); heptane, 2-methylhexane, 3-methylhexane, 2,3-dimethylpentane, 2,4-dimethylpentane, methylcyclohexane, which have 7 carbon atoms (referred to as "heptanes"); octane, 2,2,3-trimethylpentane, isooctane, ethylcyclohexane, which have 8 carbon atoms (referred to as octanes); and a mixture of these. In particular, the above heptanes are particularly preferred since they have a tendency to show a very high protection effect against oxidization, and heptane is most preferred.

The aromatic hydrocarbons are not particularly restricted, but generally they contain 6 to 20 carbon atoms, preferably 6 to 12 carbon atoms, and more preferably 7 to 10 carbon atoms. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, etc. Preferred are toluene, xylene, o-xylene, m-xylene, p-xylene, ethylbenzene, cumene, mesitylene, tetralin, butylbenzene, p-cymene, cyclohexylbenzene, diethylbenzene and pentylbenzene. More preferred are toluene, xylene, o-xylene, m-xylene, p-xylene, cumene and tetralin, and most preferred is cumene.

The halogenated hydrocarbons are not particularly restricted, and may be cyclic or acyclic, or saturated or unsaturated. However, acyclic halogenated hydrocarbons are preferably used. More preferred are chlorinated hydrocarbons and fluorinated hydrocarbons, and chlorinated hydrocarbons are still more preferred. Additionally, ones containing 1 to 6 carbon atoms, preferably 1 to 4 carbon atoms, and more preferably 1 to 2 carbon atoms are used.

As specific examples, for example, there may be mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, etc. Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane. More preferred are dichloromethane, chloroform, 1,2-dichloroethylene, trichloroethylene, chlorobenzene and 1,1,1,2-tetrafluoroethane. Still more preferred are dichloromethane, chloroform, 1,2-dichloroethylene and trichloroethylene.

The fatty acid esters are not particularly restricted, but there maybe mentioned, for example, propionates, acetates, formates, etc. Preferred are acetates and formates, and more preferred are acetates. Ester functional groups thereof are not particularly restricted, but there may be mentioned alkyl esters having 1 to 8 carbon atoms, aralkyl esters having 1 to 8 carbon atoms, etc. Preferred are alkyl esters having 1 to 6 carbon atoms, and more preferred are alkyl esters having 1 to 4 carbon atoms.

As the propionates, there may be mentioned, for example, methyl propionate, ethyl propionate, butyl propionate, isopentyl propionate, etc. Preferred is ethyl propionate.

As the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, etc. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate. More preferred are methyl acetate, ethyl acetate, propyl acetate, isopropyl acetate, butyl acetate and isobutyl acetate. Most preferred is ethyl acetate.

As the formates, there may be mentioned, for example, methyl formate, ethyl formate, propyl formate, isopropyl formate, butyl formate, isobutyl formate, sec-butyl formate, pentyl formate, etc. Preferred are methyl formate, ethyl formate, propyl formate, butyl formate, isobutyl formate and pentyl formate, and most preferred is ethyl formate.

The ethers are not particularly restricted, and may be cyclic or acyclic, or saturated or unsaturated. But saturated ones are preferably used. Generally, ones containing 3 to 20 carbon atoms, and preferably 4 to 12 carbon atoms and more preferably 4 to 8 carbon atoms are used.

As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether, etc.

Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether. More preferred are diethyl ether, methyl tert-butyl ether, anisol, dioxane, tetrahydrofuran, ethylene glycol monomethyl ether and ethylene glycol monoethyl ether. More preferred are diethyl ether, methyl tert-butyl ether, anisol, etc., and most preferred is methyl tert-butyl ether.

The nitriles are not particularly restricted, and may be cyclic or acyclic, or saturated or unsaturated. However, saturated ones are preferably used. Generally, ones containing 2 to 20 carbon atoms, preferably 2 to 12 carbon atoms, and more preferably 2 to 8 carbon atoms are used.

As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, etc.

Preferred are acetonitrile, propiononitrile, butyronitrile, isobutyronitrile, succinonitrile, valeronitrile, chloropropiononitrile, methyl cyanoacetate, ethyl cyanoacetate, tolunitrile and benzonitrile. More preferred are acetonitrile, propiononitrile, butyronitrile and isobutyronitrile, and most preferred is acetonitrile.

In selecting the solvent to be used from among the solvents mentioned above, such properties as boiling point and viscosity are preferably taken into consideration; for example, the solvent should have a boiling point which allows appropriate warming for increasing the solubility and facilitates a solvent removal from wet masses by drying and solvent recovery from crystallization filtrates (about 30 to 150° C. at 1 atm), a melting point such that solidification hardly occurs in handling at room temperature as well as upon cooling to room temperature or below (not higher than about 20° C., preferably not higher than about 10° C., still more preferably not higher than about 0° C.), and a low viscosity (not higher than about 10 cp at 20° C.). From the industrial operation viewpoint, a solvent which is scarcely volatile at ordinary temperature is preferred; for example, one having a boiling point of not lower than about 80° C. is preferred, and one having a boiling point of not lower than about 90° C. is more preferred.

Reduced coenzyme $Q_{10}$, when in a dissolved state, tends to become more resistant to oxidation as the concentration thereof increases. Reduced coenzyme $Q_{10}$ is highly soluble in the solvents mentioned above and, in this respect, too, the above solvents are suitable for the protection from oxidation. The concentration of reduced coenzyme $Q_{10}$ which is preferred from the viewpoint of protection thereof from oxidation may vary depending on the solvent species, among others, hence cannot be absolutely specified. Generally, however, the concentration of reduced coenzyme $Q_{10}$ in the above solvents is generally not lower than 1 w/w %, preferably not lower than 2 w/w %. The upper limit is not particularly restricted but, from the practical operability viewpoint, it is 400 w/w % or below, preferably 200 w/w % or below, more preferably 100 w/w % or below, still more preferably 50 w/w % or below.

Furthermore, the solubility of reduced coenzyme $Q_{10}$ in the solvents mentioned above shows a favorable temperature dependency. Therefore, the use of the above solvents is suitable also for favorably reducing the amount of reduced coenzyme $Q_{10}$ in solution and converting (crystallizing) the same into a crystalline state.

Thus, when such a solvent as mentioned above is used, it is possible to minimize the undesirable oxygen-involving side reaction in the step of reduction reaction of oxidized coenzyme $Q_{10}$ and/or crystallization of reduced coenzyme $Q_{10}$. In addition, when reduced coenzyme $Q_{10}$ is handled in the form of a solution in any of the solvents mentioned above, the reduced coenzyme $Q_{10}$ is protected from oxidation by molecular oxygen and is thus stabilized, so that such handling operations as extraction and washing (extraction using any of the above solvents as added from the outside and washing with water), concentration (including solvent substitution by adding another solvent while concentrating) and column chromatography may be carried out successfully. In the practice of the invention, it is of course preferred that the series of operations from the reduction reaction of oxidized coenzyme $Q_{10}$ to the crystallization (purification by crystallization) of reduced coenzyme $Q_{10}$ (inclusive of extraction of reduced coenzyme $Q_{10}$ washing the extract with water, and so forth, where necessary) be carried out using the solvent or solvents mentioned above.

In the practice of the invention, the above solvents may be used in combination with another solvent, if necessary, within such an amount that the latter does not produce some or other adverse effect. For example, an appropriate amount of another solvent may be added to the above solvents in order to improve the solubility of oxidized coenzyme $Q_{10}$ and/or reduced coenzyme $Q_{10}$, the solubility of the reducing agent, the rate of reaction and the like in the reduction reaction and, in the crystallization of reduced coenzyme $Q_{10}$, to improve the solubility of reduced coenzyme $Q_{10}$ as well as the crystallization concentration, crystallization temperature, yield, slurry properties, crystal properties, and the like.

Such other solvent is not particularly restricted but includes, among others, water, alcohols, fatty acids, ketones, nitrogen-containing compounds other than nitriles, and sulfur-containing compounds, and the like.

The alcohols are not particularly restricted but may be cyclic or acyclic, or saturated or unsaturated. Saturated ones are preferred, however. Generally, they contain 1 to 20 carbon atoms, preferably 1 to 12 carbon atoms, more preferably 1 to 6 carbon atoms, still more preferably 1 to 5 carbon atoms, and most preferably 1 to 3 carbon atoms. Monohydric alcohols containing 2 or 3 carbon atoms, dihydric alcohols containing 2 to 5 carbon atoms, and the trihydric alcohol containing 3 carbon atoms are preferred, among others.

As the monohydric alcohol, there may be mentioned, for example, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, etc.

Preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol and cyclohexanol. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol and neopentyl alcohol. Still more preferred are methanol, ethanol, 1-propanol, 2-propanol, 1-butanol, 2-butanol, isobutyl alcohol, 2-methyl-1-butanol and isopentyl alcohol. Further preferred are methanol, ethanol, 1-propanol and 2-propanol, particularly preferred are ethanol, 1-propanol and 2-propanol, and most preferred is ethanol.

As the dihydric alcohol, there may be mentioned, for example, 1,2-ethanediol, 1,2-propandiol, 1,3-propandiol, 1,2-butanediol, 1,3-butanediol, 1,4-butanediol, 2,3-butanediol, 1,5-pentanediol, etc. Preferred are 1,2-ethanediol, 1,2-propandiol and 1,3-propandiol, and most preferred is 1,2-ethanediol.

As the trihydric alcohol, glycerol, etc. may be preferably used, for example.

As fatty acids, there may be mentioned, for example, formic acid, acetic acid, propionic acid, etc. Preferred are formic acid and acetic acid, and most preferred is acetic acid.

The ketones are not particularly restricted, and ones having 3 to 6 carbon atoms are preferably used. As specific examples, there may be mentioned, for example, acetone, methyl ethyl ketone, methyl butyl ketone, methyl isobutyl ketone, etc. Preferred are acetone and methyl ethyl ketone, and most preferred is acetone.

As the nitrogen compounds, there may be mentioned, for example, nitromethane, triethylamine, pyridine, formamide, N-methylformamide, N,N-dimethylformamide, N,N-dimethylacetoamide, N-methylpyrrolidone, etc.

As the sulfur compounds, there may be mentioned, for example, dimethyl sulfoxide, sulfolane, etc.

It is recommended that the above-mentioned other solvent is used, together with at least one solvent selected from among hydrocarbons, fatty acid esters, ethers, and nitrites, in an adequate proportion depending on the solvent characteristics thereof, including the known physical properties thereof, such as melting point, boiling point, vapor pressure characteristics, and phase transition, and the above-mentioned solvent amount and, further, on the effect to the solubility of oxidized coenzyme $Q_{10}$, reduced coenzyme $Q_{10}$ and/or the reducing agent.

Although the other solvent may be used within an amount causing no adverse effect, without any other particular restriction, it is preferred from the viewpoint of oxidation-protective effect and/or crystallization yield (to be mentioned later herein), among others, that the above-mentioned solvent with high oxidation-protective effect (at least one species selected from among hydrocarbons, fatty acid esters, ethers, and nitrites) is present in a larger proportion. It is more preferred to use a solvent whose substantial main ingredient is a solvent with high oxidation-protective effect.

In cases where the system comprises a homogeneous solvent phase, at least one solvent selected from among hydrocarbons, fatty acid esters, ethers, and nitrites is preferably used as the reaction solvent or crystallization solvent or as the main ingredient of the solvent for handling in the concentration, extraction, column chromatography and/or other operations. In cases where the system forms different solvent phases, it is a preferred embodiment that the main ingredient of the solvent phase having larger solubility of reduced coenzyme $Q_{10}$ (in the case of a mixed solvent system composed of water and an organic solvent low in miscibility with water, for instance, reduced coenzyme $Q_{10}$ is scarcely soluble in the aqueous phase but soluble in the organic solvent phase low in miscibility with water) is at least one solvent selected from among hydrocarbons, fatty acid esters, ethers, and nitrites.

From such viewpoint, the other solvent is used generally in a volume ratio of lower than about 0.3, preferably lower than about 0.2, more preferably lower than about 0.1, and still more preferably lower than about 0.05, relative to the whole solvent amount in the case of homogeneous systems or, in the case of heterogeneous systems, to the volume of the solvent having larger solubility of reduced coenzyme $Q_{10}$. Needless to say, the lower limit is 0 (zero).

Among the other solvents specifically given hereinabove, alcohols and/or water are most preferably used either singly or in combination from the reaction rate and yield improvement viewpoint in the reduction reaction of oxidized coenzyme $Q_{10}$. In the step of crystallizing reduced coenzyme $Q_{10}$, water can be preferably used from the viewpoint of improvement in slurry characteristics such as fluidity.

Now, a method of producing reduced coenzyme $Q_{10}$ by reducing oxidized coenzyme $Q_{10}$ is described.

The oxidized coenzyme $Q_{10}$ to be used in the practice of the invention may be one prepared by synthesis, fermentation, or extraction from a natural product, for instance, as mentioned hereinabove, or may be an existing high-purity grade of coenzyme $Q_{10}$. It may consist of oxidized coenzyme $Q_{10}$ alone or may be a mixture of oxidized coenzyme $Q_{10}$ and reduced coenzyme $Q_{10}$.

In the practice of the invention, the reduction of oxidized coenzyme $Q_{10}$ is carried out using, as a solvent, the above-mentioned solvent with high oxidation-protective effect, namely at least one species selected from among hydrocarbons, fatty acid esters, ethers, and nitriles, and, as the reducing agent, a metal hydride compound, iron (metallic iron or iron in a salt form), zinc (metallic zinc), dithionous acid or a salt thereof, or ascorbic acid or a related compound thereof for instance.

The metal hydride compound is not particularly restricted but includes, among others, sodium borohydride and lithium aluminum hydride. The amount to be used of the metal hydride compound may vary depending on the species thereof, hence cannot be absolutely specified. Generally, however, the reduction can be favorably carried out by using it in an amount of 1 to 3 times the theoretical hydrogen equivalent.

The reduction using iron or zinc is generally carried out using an acid. The acid is not particularly restricted but includes, among others, fatty acids such as acetic acid, sulfonic acids such as methanesulfonic acid, and inorganic acids such as hydrochloric acid and sulfuric acid. Inorganic acids are preferred, and sulfuric acid is more preferred.

The amount of iron to be used is not particularly restricted but, for example, an amount of about ⅕ by weight or larger based on the charged weight of oxidized coenzyme $Q_{10}$ is appropriate for carrying out the reaction. The upper limit is not particularly restricted but, from the economical viewpoint, it is about twice the weight of the above charged weight or lower. Iron may be used not only in the form of metallic iron but also in the form of a salt, for example iron(II) sulfate, etc.

The amount of zinc to be used is not particularly restricted but, for example, an amount of about ⅒ by weight or larger based on the charged weight of oxidized coenzyme $Q_{10}$ is appropriate for carrying out the reaction. The upper limit is not particularly restricted but, from the economic viewpoint, it is about twice the weight of the above charged weight or lower.

The dithionous acid or a salt thereof is not particularly restricted but a salt form of dithionous acid is generally used. The salt of dithionous acid is not particularly restricted but includes, as preferred species, alkali metal salts, alkaline earth metal salts, ammonium salt and the like. Alkali metal salts such as the lithium salt, sodium salt, and potassium salt are more preferred, and the sodium salt is most preferred. The amount to be used of the dithionous acid or salt is not particularly restricted but it is generally not smaller than about ⅕ by weight, preferably not smaller than about ⅖ by weight, and more preferably not smaller than about ⅗ by weight, based on the charged weight of oxidized coenzyme $Q_{10}$. Larger amounts may be used without causing any particular trouble. From the economical viewpoint, however, the amount to be employed is not larger than about twice the weight of the above-mentioned charged weight, preferably not larger than the charged weight. Thus, the reaction can be more favorably carried out with employing an amount within the range of about ⅖ by weight of the above-mentioned charge to a weight roughly equal to that of the charged weight.

The ascorbic acid or related compounds thereof are not particularly restricted, and include, for example, not only ascorbic acid, but also rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, and the like ascorbic acid derivatives, and may be ester forms or salts of these. Furthermore, these may be L-form, D-form or racemic form. More specifically, there may be mentioned, for example, L-ascorbic acid, L-ascorbyl palmitate, L-ascorbyl stearate, D-arabo-ascorbic acid, etc. In producing the reduced coenzyme $Q_{10}$, any of the above-mentioned ascorbic acid and related compounds thereof may be suitably used. However, the water-soluble ones are suitably used in particular among the above-mentioned ascorbic acid or related compounds thereof in view of separatability with the generated reduced coenzyme $Q_{10}$, etc. And most preferred is a free form of L-ascorbic acid, D-arabo-ascorbic acid, and the like in view of the ready availability, price, etc.

The amount to be used of the ascorbic acid or a related compound thereof mentioned above is not particularly restricted but may be an amount effective in converting oxidized coenzyme $Q_{10}$ to reduced coenzyme $Q_{10}$. Generally it is not smaller than 1 mole, preferably not smaller than 1.2 moles, per mole of oxidized coenzyme $Q_{10}$. The upper limit is not particularly restricted but, from the economical viewpoint, it is generally not higher than 10 moles, preferably not higher than 5 moles, and more preferably not higher than 3 moles, per mole of the oxidized coenzyme $Q_{10}$.

Among the reducing agent species mentioned above, zinc, dithionous acid and salts thereof, and ascorbic acid and related compounds thereof are preferred from the viewpoint of reducing ability, yield and/or quality, among others, and, in particular, dithionous acid (specifically dithionous acid salts) and ascorbic acid or related compounds thereof are preferred.

In carrying out the reduction reaction, an alcohol and/or water are/is suitably used singly or in combination, as mentioned above. Water is preferred in particular when iron, zinc, or dithionous acid or a salt thereof is used as the reducing agent. When a metal hydride compound or ascorbic acid or a related compound thereof is used as the reducing agent, an alcohol can be used in combination. The combined use of water and an alcohol exhibits the characteristics of both water and the alcohol and contributes to improvements in reaction rate and yield, among others.

In the following, a preferred method of reduction is described in detail.

The reduction using dithionous acid or a salt thereof is preferably carried out using water in combination, namely in a mixed solvent system composed of at least one organic solvent selected from among the above-mentioned hydrocarbons, fatty acid esters, ethers, and nitriles, with water. On that occasion, the reaction is preferably carried out generally at a pH of not higher than 7, preferably at pH 3 to 7, more preferably at pH 3 to 6, from the viewpoint of yield, etc. The pH can be adjusted using an acid (e.g. an inorganic acid such as hydrochloric acid or sulfuric acid) or a base (e.g. an alkali metal hydroxide such as sodium hydroxide).

In the reduction using dithionous acid or a salt thereof, the amount of water is not particularly restricted but may be an amount of water such that an appropriate amount of the reducing agent, namely dithionous acid or a salt thereof, can be dissolved therein. Thus, for example, it is advisable that the amount of the dithionous acid or a salt be adjusted generally to not more than 30 w/w %, and preferably not more than 20 w/w %, relative to the weight of water. From the productivity viewpoint, among others, it is advisable that the amount be adjusted generally to not less than 1 w/w %, preferably not less than 5 w/w %, and more preferably not less than 10 w/w %.

The reduction using the ascorbic acid or a related compound thereof mentioned above is preferably carried out using a solvent especially highly miscible with water as selected from among the above-mentioned hydrocarbons, fatty acid esters, ethers, and nitrites, in particular at least one species selected from among ethers and nitriles, which are highly miscible with water, and more specifically tetrahydrofuran, dioxane, acetonitrile or the like. An alcohol may also be used as another solvent. Furthermore, from the viewpoint of reaction promotion (e.g. reaction temperature lowering or reaction time shortening) in the production of reduced coenzyme $Q_{10}$, it is also possible to carry out the reduction in the presence of an additive having a reaction promoting effect, such as a basic substance or a hydrogensulfite.

The basic compound is not particularly restricted but may be either an inorganic compound or an organic compound. The inorganic compound is not particularly restricted but includes, among others, the hydroxides, carbonates, and hydrogencarbonates of metals (preferably alkali metals, alkaline earth metals, and the like), and ammonia. As typical examples thereof, there may be mentioned alkali metal hydroxides such as sodium hydroxide, alkali metal carbonates such as sodium carbonate, alkali metal hydrogencarbonates such as sodium hydrogencarbonate, and alkaline earth metal carbonates such as magnesium carbonate. The organic compound is not particularly restricted but includes, among others, amines such as triethylamine. Among the basic substances specifically mentioned above, weakly basic substances (weak bases or weak alkalis) such as the carbonates and hydrogencarbonates of metals (preferably alkali metals, alkaline earth metals, etc.), ammonia, and like inorganic compounds; amines such as triethylamine, and like organic compounds are preferably used. More preferred are the weakly basic inorganic compounds mentioned above.

Preferred as the hydrogensulfite are, for example, alkali metal hydrogensulfites such as sodium hydrogensulfite.

The amount of the additive mentioned above is not particularly restricted but may be such that the reaction promoting effect of the additive can be produced to a desired extent (effective amount). From the economical viewpoint, however, the amount is generally not more than 20 moles, preferably not more than 10 moles, more preferably not more than 5 moles, and still more preferably not more than 2 moles, per mole of the ascorbic acid or a related compound thereof. The lower limit is not particularly restricted but, generally, it is not less than 0.01 moles, preferably not less than 0.05 moles, more preferably not less than 0.1 moles, and still more preferably not less than 0.2 moles, per mole of the ascorbic acid or a related compound thereof.

In the practice of the invention, the reduction reaction is preferably carried out under forced flowing. The power required for stirring to cause such flowing per unit volume is generally not less than about 0.01 kW/$m^3$, preferably not less than about 0.1 kW/$m^3$, and more preferably not less than about 0.3 kW/$m^3$. The above forced flowing is generally caused by the turning of a stirring blade(s). The use of a stirring blade(s) is not always necessary if the above flowing can be otherwise obtained. For example a method based on liquid circulation may be utilized.

The reduction temperature may vary depending on the reducing agent species and/or amount, hence cannot be absolutely specified. In the reduction using dithionous acid or a salt thereof, for instance, the reduction is generally carried out at 100° C. or below, preferably at 80° C. or below, more preferably at 60° C. or below. The lower limit is the solidification temperature of the system. Thus, the reduction can be favorably carried out generally at about 0 to 100° C., preferably at about 0 to 80° C., more preferably at about 0 to 60° C. In the reduction using ascorbic acid or a related compound thereof, the reduction is carried out generally at 30° C. or higher, preferably at 40° C. or higher, more preferably at 50° C. or higher. The upper limit is the boiling point of the system. Thus, the reduction can be favorably carried out generally at about 30 to 150° C., preferably about 40 to 120° C., more preferably at about 50 to 100° C.

The reaction concentration is not particularly restricted but the weight of oxidized coenzyme $Q_{10}$ relative to the solvent weight is generally not less than about 1 w/w %, preferably not less than 3 w/w %, more preferably not less than 10 w/w %, and still more preferably not less than 15 w/w %. The upper limit is not particularly restricted but generally is not higher than about 60 w/w %, preferably not higher than 50 w/w %, more preferably not higher than 40 w/w %, and still more preferably not higher than 30 w/w %. Thus, the reaction can be favorably carried out at a reaction concentration of about 1 to 60 w/w %, preferably about 3 to 50 w/w %, and more preferably about 10 to 40 w/w %.

The reduction reaction time may vary depending on the reducing agent species and/or the amount thereof, hence cannot be absolutely specified. Generally, however, the reaction can be driven to completion within 48 hours, preferably within 24 hours, more preferably within 10 hours, and still more preferably within 5 hours.

It is exceedingly preferable to carry out the reduction reaction in a deoxidized atmosphere. Surprisingly, it was found that, in the reduction reaction using dithionous acid or a salt thereof, in particular, such atmosphere greatly contributes to an improvement in reduction reaction yield and a reduction in reducing agent amount. The deoxidized atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, and carbon dioxide gas. Nitrogen gas is preferred, however.

An organic phase containing the product reduced coenzyme $Q_{10}$ is recovered from the thus-obtained reduction reaction mixture and, if necessary (preferably), the organic phase is further washed repeatedly using water, an aqueous solution of sodium chloride, or the like to achieve complete contaminant elimination and, then, it can be subjected to crystallization. When the dithionous acid or a salt thereof mentioned above, such as sodium dithionite, in particular, is used as the reducing agent, it is desirable to repeat washing with water so that contaminants derived from the dithionous acid or salt thereof may be removed completely and/or the pH of the aqueous phase may be stabilized.

When oxidized coenzyme $Q_{10}$ is reduced with ascorbic acid or a related compound thereof using the above-mentioned highly water-miscible solvent, in particular at least one species selected from among those ethers and nitrites which are highly miscible with water (e.g. tetrahydrofuran, dioxane, acetonitrile, etc.), it is a very convenient and efficient procedure to crystallize reduced coenzyme $Q_{10}$ directly from the reduction reaction mixture (direct isolation method (one-pot method)).

The above treatment following the reduction reaction is preferably carried out in a deoxidized atmosphere and, thereby, the oxidation-protective effect can be further increased.

The crystallization of reduced coenzyme $Q_{10}$ is now described.

The reduced coenzyme $Q_{10}$ to be subjected to crystallization can be obtained in the conventional manner, for example, by synthesis, fermentation, or extraction from a natural source. Preferred is the product obtained by reduction of oxidized coenzyme $Q_{10}$ contained in reduced coenzyme $Q_{10}$, or reduction of oxidized coenzyme $Q_{10}$. More preferred is the product obtained by carrying out the reduction reaction in accordance with the present invention, as described above.

While the method of crystallization according to the invention can be applied also to products containing oxidized coenzyme $Q_{10}$ in relatively large amounts, the method is particularly effective in crystallizing high-purity reduced coenzyme $Q_{10}$ prepared by the reduction method described above. In the practice of the invention, it is very effective to purify and crystallize reduced coenzyme $Q_{10}$ with simultaneous removal of impurities contained in the reaction mixture or extract obtained in the conventional manner or produced by the above-mentioned reduction method or the like. More specifically, reduced coenzyme $Q_{10}$ can be crystallized from the reduction reaction mixture obtained by the reduction method mentioned above, or a solution obtained by collecting the reduced coenzyme $Q_{10}$-containing organic phase from the above reaction mixture, if necessary followed by washing of the organic phase. On that occasion, the impurities should preferably be eliminated into the mother liquor. This makes it possible to remove coexisting impurities, in particular analogous compounds having a similar structure and generally not always easy to remove (specifically, reduced coenzyme $Q_9$, reduced coenzyme $Q_8$, reduced coenzyme $Q_7$, etc.). Needless to say, it is possible to utilize the method as a method of recrystallizing reduced coenzyme $Q_{10}$ crystals obtained beforehand by purification and crystallization.

The crystallization of reduced $Q_{10}$ is carried out using, as the solvent, at least one species selected from among the above-mentioned hydrocarbons, fatty acid esters, ethers, and nitrites. Among them, hydrocarbons are preferred, aliphatic hydrocarbons and aromatic hydrocarbons are more preferred, aliphatic hydrocarbons are still more preferred, and the above-mentioned pentanes, hexanes, heptanes and octanes are most preferred. From the viewpoint of crystallization yield and/or unnecessariness of excessive cooling in crystallization, among others, acyclic aliphatic hydrocarbons are particularly preferred among the aliphatic hydrocarbons.

The method of crystallization is not particularly restricted but the crystallization can be carried out by utilizing a conventional crystallization method, namely at least one of the cooling crystallization, concentration crystallization, solvent substitution crystallization and other methods. In particular, the cooling crystallization method, or a combination of the cooling crystallization method with some other method of crystallization is preferred.

The cooling temperature in the step of crystallization is an important factor and, from the yield viewpoint, among others, it is generally not higher than 20° C., preferably not higher than 10° C., more preferably not higher than 5° C. The lower limit is the solidification temperature of the system. Thus, the crystallization can be advantageously carried out generally at a cooling temperature of about −30° C. to +10° C., preferably about −20° C. to +10° C., more preferably about −10° C. to +5° C.

In the process of crystallization, the amount of crystals crystallizing out per unit time may be controlled to minimize the immixture of various impurities into the obtained reduced coenzyme $Q_{10}$, or to obtain a slurry with good characteristics. A preferred rate of crystallization per unit time is, for example, not higher than the rate of crystallization which causes crystallization of about 50%, per unit time, of the whole amount of crystals to be obtained (i.e. at most 50%/hour), preferably not higher than the rate of crystallization which causes crystallization of about 25%, per unit time, of the whole amount of crystals to be obtained (i.e. at most 25%/hour). The rate of cooling in the crystallization by cooling is generally not higher than about 40° C./hour, and preferably not higher than about 20° C./hour.

The crystallization concentration is also an important factor and, when expressed in terms of the weight of reduced coenzyme $Q_{10}$ relative to the weight of the crystallization solvent at the time of completion of crystallization, it is not higher than about 15 w/w %, preferably not higher than about 13 w/w %, more preferably not higher than 10 w/w %. The preferred crystallization concentration may vary depending on the solvent species employed and, for attaining satisfactory crystallization results using an aliphatic hydrocarbon or a solvent whose main ingredient is an aliphatic hydrocarbon, the crystallization concentration is not higher than about 13 w/w %, preferably not higher than about 10 w/w %, more preferably not higher than about 8 w/w % and, in the case of an acyclic aliphatic hydrocarbon, which is most preferred, or a solvent whose main ingredient is an acyclic aliphatic hydrocarbon, the crystallization concentration is not higher than about 10 w/w %, preferably not higher than about 8 w/w %, and more preferably not higher than about 7 w/w %. By maintaining such a concentration as mentioned above, it becomes possible to carry out the crystallization favorably in a manner adapted to the operability on an industrial scale. The lower limit to the crystallization concentration is not particularly restricted but, from the productivity viewpoint, it is generally not lower than about 1 w/w %, preferably not lower than about 2 w/w %.

The crystallization is preferably carried out under forced flowing. For preventing the state of supersaturation from occurring and thereby allowing the nucleation and crystal growth to proceed smoothly and, furthermore, from the viewpoint of obtaining high-quality products, the flowing is generally brought about by a stirring power per unit volume of not weaker than about 0.01 $kW/m^3$, preferably not weaker than about 0.1 $kW/m^3$, and more preferably not weaker than about 0.3 $kW/m^3$. The forced flowing is generally provided by the turning of a stirring blade(s). However, the use of a stirring blade(s) is not always necessary if the above flowing can be otherwise obtained. For example, it is possible to utilize a method based on liquid circulation.

In carrying out the crystallization, seed crystals are preferably added so that the state of supersaturation may be prevented from occurring and the nucleation and crystal growth may be allowed to proceed smoothly.

In carrying out the crystallization according to the invention, such another auxiliary solvent as mentioned above may be used, according to need, in combination with the above-mentioned solvent having a high protective effect against oxidation if the other solvent will not produce any adverse effect. While an appropriate amount of such other auxiliary solvent may be added to the solvent mentioned above for improving the solubility of reduced coenzyme $Q_{10}$ as well as the crystallization concentration, crystallization temperature, yield, slurry characteristics, and crystal characteristics, among others, the use of such a mixed solvent may result in a drastic increase in solubility, whereby the crystallization yield rather tends to decrease in some instances. Therefore, from the viewpoint of oxidation-protective effect and/or crystallization yield, among others, a solvent, whose substantial main ingredient is the solvent mentioned above, is preferably used. Thus, when the solvent is used in admixture with another solvent, the proportion (ratio by volume) of the other solvent is not particularly restricted but generally is not higher than about 0.3, preferably not higher than about 0.2, more preferably not higher than about 0.1, and still more preferably not higher than about 0.05. Needless to say, the lower limit is 0 (zero). As mentioned hereinabove, the volume ratio is the proportion of the volume of the other solvent to the whole solvent volume in the case of homogeneous systems and, in the case of heterogeneous systems, the proportion of the volume of the other solvent(s) to the volume of the solvent phase in which reduced coenzyme $Q_{10}$ is well soluble.

When water is used combinedly as the other auxiliary solvent, however, water can show its characteristics and can contribute to improvements in slurry characteristics, for instance. The amount of water in the crystallization of reduced coenzyme $Q_{10}$ influences on the slurry concentration of reduced coenzyme $Q_{10}$ crystallized out and/or on the slurry characteristics. As the amount of water increases, the slurry concentration decreases and the fluidity generally increases. On the other hand, the decrease in slurry concentration as a whole leads to a decrease in productivity. The amount of water is not particularly restricted but, taking the above factors into consideration, it may be varied so that it may be adjusted to and maintained in an appropriate range.

The other auxiliary solvent mentioned above may be added prior to or during the crystallization process or after stabilization of the amount of the precipitated crystals.

The thus-obtained crystals of reduced coenzyme $Q_{10}$ can be recovered as a wet product, for example, by such a solid-liquid separation technique as centrifugation, pressure filtration, or vacuum filtration, if necessary followed by cake washing. They can be recovered also as a dry product by further charging the wet product in a reduced pressure drier (vacuum drier) internally purged with an inert gas and drying the same under reduced pressure. The recovery in a dry form is preferred.

When the crystallization is carried out in a deoxidized atmosphere, the protective effect against oxidation can be further increased. The deoxidized atmosphere can be attained by inert gas substitution, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, and carbon dioxide gas. Nitrogen gas is preferred, however.

In accordance with the present invention, high-quality reduced coenzyme $Q_{10}$ can be synthesized and crystallized in a convenient and efficiency manner. The crystals of reduced coenzyme $Q_{10}$ as obtained in accordance with the present invention are of very high quality and can be expected to have a reduced coenzyme $Q_{10}$/oxidized coenzyme $Q_{10}$ weight ratio of not lower than 96/4, preferably not lower than 98/2, more preferably not lower than 99/1.

BEST MODE FOR CARRYING OUT THE INVENTION

The following examples illustrate the present invention in further detail. These examples are, however, by no means limitative of the scope of the present invention. In the examples, the purity of reduced coenzyme $Q_{10}$ and the reduced coenzyme $Q_{10}$/oxidized coenzyme $Q_{10}$ weight ratio were determined by the HPLC analysis specified below. The reduced coenzyme $Q_{10}$ purity values as determined, however, are by no means indicative of the limit purity value attainable in accordance with the present invention. Likewise, the reduced coenzyme $Q_{10}$/oxidized coenzyme $Q_{10}$ weight ratio values obtained never indicate the upper limit to that ratio.

(HPLC Conditions)

Column: SYMMETRY C18 (product of Waters), 250 mm (in length), 4.6 mm (in inside diameter); mobile phase: $C_2H_5OH:CH_3OH=4:3$ (v/v); detection wavelength: 210 nm; flow rate: 1 ml/min; retention time of reduced coenzyme $Q_{10}$: 9.1 min; retention time of oxidized coenzyme $Q_{10}$: 13.3 min.

EXAMPLE 1

Oxidized coenzyme $Q_{10}$ (100 g; containing 0.40% of oxidized coenzyme $Q_9$, purity 99.4%) was dissolved in 1000 g of heptane at 25° C. While stirring (power required for stirring: 0.3 kW/m$^3$), an aqueous solution prepared by dissolving 100 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the heptane phase was washed 6 times with 1000 g of a deaerated saturated aqueous sodium chloride solution to give a heptane phase containing 100 g of reduced coenzyme $Q_{10}$ (containing 0.40% of reduced coenzyme $Q_9$). This heptane phase was cooled to 2° C. while stirring (power required for stirring: 0.3 kW/m$^3$) to give a white slurry. All the above operations were carried out in a nitrogen atmosphere. The slurry obtained was filtered under reduced pressure, and the wet crystals were washed in sequence with cold heptane, cold ethanol, cold water, cold ethanol and cold heptane (the cold solvents used for washing having a temperature of 2° C.). The wet crystals were further dried under reduced pressure (20–40° C., 1–30 mmHg) to give 93 g of white dry crystals (containing 0.29% of reduced coenzyme $Q_9$, percentage of elimination: 28%)(isolated product yield: 93 mole percent). The reduced coenzyme $Q_{10}$/oxidized coenzyme $Q_{10}$ weight ratio of the crystals obtained was 99.6/0.4, and the purity of the reduced coenzyme $Q_{10}$ was 99.2%.

EXAMPLE 2 AND COMPARATIVE EXAMPLE 1

One gram of the reduced coenzyme $Q_{10}$ obtained in Example 1 was dissolved in 20 g of each of various solvents shown in Table 1 at 25° C. After 24 hours of stirring in the air at 25° C., the reduced coenzyme $Q_{10}$/oxidized coenzyme $Q_{10}$ weight ratio in each solution was determined. The results thus obtained are shown in Table 1 together with the results obtained by storing the crystal under the same conditions as above (1 g of reduced coenzyme $Q_{10}$ stored in the air at 25° C. for 24 hours) for comparison.

TABLE 1

| | | R |
|---|---|---|
| Example 2 | Heptane | 99.1/0.9 |
| | Hexane | 98.7/1.3 |
| | Toluene | 98.8/1.2 |
| | Chloroform | 98.9/1.1 |
| | Ethyl acetate | 98.9/1.1 |
| | Methyl tert-butyl ether | 98.6/1.4 |
| | Tetrahydrofuran | 98.5/1.5 |
| Comparative Example 1 | Methyl isobutyl ketone | 69.2/30.8 |
| | Dimethylformamide | 31.0/69.0 |
| | N-Methylpyrrolidone | 67.3/32.7 |
| | Crystal | 95.9/4.1 |

R: Reduced coenzyme $Q_{10}$/oxidized coenzyme $Q_{10}$ weight ratio

EXAMPLE 3 AND COMPARATIVE EXAMPLE 2

One gram of the reduced coenzyme $Q_{10}$ obtained in Example 1 was dissolved in 100 g of each of various solvents shown in Table 2 at 35° C. After 24 hours of stirring at 35° C. in the air, the reduced coenzyme $Q_{10}$/oxidized coenzyme $Q_{10}$ weight ratio in each solution was determined. The results thus obtained are shown in Table 2.

TABLE 2

| | Solvent | R |
|---|---|---|
| Example 3 | Heptane | 96.7/3.3 |
| | Ethyl acetate | 96.4/3.6 |
| | Acetonitrile | 96.0/4.0 |

TABLE 2-continued

| | Solvent | R |
|---|---|---|
| Comparative Example 2 | Methyl isobutyl ketone | 46.1/53.9 |

R: Reduced coenzyme $Q_{10}$/oxidized coenzyme $Q_{10}$ weight ratio

EXAMPLE 4

Ten grams of oxidized coenzyme $Q_{10}$ was dissolved in 100 g of each of various solvents shown in Table 3 at 25° C. While stirring (power required for stirring: 0.3 kW/m$^3$), an aqueous solution prepared by dissolving 10 g of a commercial grade of sodium dithionite (purity: at least 75%), as the reducing agent, in 100 ml of water was gradually added and the reduction reaction was carried out at 25° C. and at pH 4 to 6. After the lapse of 2 hours, the aqueous phase was removed from the reaction mixture, and the organic phase was washed 6 times with 100 g of a deaerated saturated aqueous sodium chloride solution. All the operations were carried out in a nitrogen atmosphere. The reduced coenzyme $Q_{10}$/oxidized coenzyme $Q_{10}$ weight ratio in the organic phase was then determined. The results thus obtained are shown in Table 3.

TABLE 3

| Solvent | R |
|---|---|
| Heptane | 99.5/0.5 |
| Hexane | 99.3/0.7 |
| Ethyl acetate | 99.4/0.6 |
| Methyl tert-butyl ether | 99.2/0.8 |
| Toluene | 99.4/0.6 |
| Chloroform | 99.3/0.7 |

R: Reduced coenzyme $Q_{10}$/oxidized coenzyme $Q_{10}$ weight ratio

EXAMPLE 5

Ten grams of oxidized coenzyme $Q_{10}$ was dissolved in 100 g of heptane at 25° C., 1.5 g of a zinc powder and 110 g of 2.9 N sulfuric acid were added and, after 6 hours of stirring (power required for stirring: 0.3 kW/m$^3$) at 25° C., 100 g of concentrated hydrochloric acid was added. The reduced coenzyme $Q_{10}$/oxidized coenzyme $Q_{10}$ weight ratio in the heptane phase was determined and found to be 99.6/0.4. All the operations were carried out in a nitrogen atmosphere.

EXAMPLE 6

The reduction reaction and crystallization were carried out in the same manner as in Example 1 except that hexane was used as the solvent for dissolving oxidized coenzyme $Q_{10}$. As a result, 93 g of dry white crystals were obtained (isolated product yield: 93 mole percent). The reduced coenzyme $Q_{10}$/oxidized coenzyme $Q_{10}$ weight ratio of the crystals obtained was 99.4/0.6, and the purity of the reduced coenzyme $Q_{10}$ was 99.0%.

EXAMPLE 7

Oxidized coenzyme $Q_{10}$ (100 g; purity 99.4%) was dissolved in 1000 g of hexane at 25° C. While stirring (power required for stirring: 0.3 kW/m$^3$), an aqueous solution prepared by dissolving 100 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the hexane phase was washed 6 times with 1000 g of a deaerated saturated aqueous sodium chloride solution. Methanol (50 g) was added to the hexane phase, and the mixture was cooled to 2° C. while stirring (power required for stirring: 0.3 kW/m$^3$) to give a white slurry. All the above operations were carried out in a nitrogen atmosphere. The slurry obtained was filtered under reduced pressure, and the wet crystals were washed in sequence with cold hexane, cold ethanol, cold water, cold ethanol and cold hexane (the cold solvents used for washing having a temperature of 2° C.). The wet crystals were further dried under reduced pressure (20–40° C., 1–30 mmHg) to give 92 g of dry white crystals (isolated product yield: 92 mole percent). The reduced coenzyme $Q_{10}$/oxidized coenzyme $Q_{10}$ weight ratio of the crystals obtained was 99.4/0.6, and the purity of the reduced coenzyme $Q_{10}$ was 99.0%.

EXAMPLE 8

Oxidized coenzyme $Q_{10}$ (100 g; purity 99.4%) was dissolved in 1000 g of ethyl acetate at 25° C. While stirring (power required for stirring: 0.3 kW/m$^3$), an aqueous solution prepared by dissolving 100 g of sodium dithionite (purity at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the ethyl acetate phase was washed 6 times with 1000 g of a deaerated saturated aqueous sodium chloride solution. Ethanol (300 g) and 50 g of water were added to the ethyl acetate phase, and the mixture was cooled to 2° C. while stirring (power required for stirring: 0.3 kW/m$^3$) to give a white slurry improved in fluidity as compared with Example 1. All the above operations were carried out in a nitrogen atmosphere. The slurry obtained was filtered under reduced pressure, and the wet crystals were washed in sequence with cold ethanol, cold water, and cold ethanol (the cold solvents used for washing having a temperature of 2° C.). The wet crystals were dried under reduced pressure (20–40° C., 1–30 mmHg) to give 89 g of dry white crystals (isolated product yield: 89 mole percent). The reduced coenzyme $Q_{10}$/oxidized coenzyme $Q_{10}$ weight ratio of the crystals obtained was 99.5/0.5, and the purity of the reduced coenzyme $Q_{10}$ was 99.2%.

EXAMPLE 9

Reduced coenzyme $Q_{10}$ (100 g; reduced coenzyme $Q_{10}$/oxidized coenzyme $Q_{10}$ weight ratio: 95/5; purity as coenzyme $Q_{10}$: 99.4%) was dissolved in 1000 g of heptane at 25° C. While stirring (power required for stirring: 0.3 kW/m$^3$), an aqueous solution prepared by dissolving 10 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the heptane phase was washed 6 times with 1000 g of a deaerated saturated aqueous sodium chloride solution. This heptane phase was cooled to 2° C. while stirring (power required for stirring: 0.3 kW/m$^3$) to give a white slurry. All the above operations were carried out in a nitrogen atmosphere. The slurry obtained was filtered under reduced pressure, and the wet crystals were washed in sequence with cold heptane, cold ethanol, cold water, cold ethanol and cold heptane (the cold solvents used for washing having a temperature of 2° C.). The wet crystals were dried under reduced pressure (20–40° C., 1–30 mmHg) to give 93 g of dry white crystals (isolated product yield: 93 mole percent). The reduced coenzyme Q10/oxidized coenzyme $Q_{10}$ weight ratio of the crystals obtained was 99.6/0.4, and the purity of the reduced coenzyme $Q_{10}$ was 99.2%.

EXAMPLE 10

The reduction reaction and crystallization were carried out under exactly the same conditions as in Example 1 except that the oxidized coenzyme $Q_{10}$ used has a purity of 98.4% (containing 1.0% of oxidized coenzyme $Q_9$, 0.30% of oxidized coenzyme $Q_8$ and 0.04% of oxidized coenzyme $Q_7$). As a result, 93 g of dry white crystals (containing 0.72% of reduced coenzyme $Q_9$, percentage of elimination: 28%; and 0.11% of reduced coenzyme $Q_8$, percentage of elimination: 63%; reduced coenzyme $Q_7$: not detected) (isolated product yield: 93 mole percent) were obtained. The reduced coenzyme $Q_{10}$/oxidized coenzyme $Q_{10}$ weight ratio of the crystals obtained was 99.6/0.4, and the purity of the reduced coenzyme $Q_{10}$ was 99.0%.

EXAMPLE 11

Ten grams of crystals of reduced coenzyme $Q_{10}$ (containing 0.29% of reduced coenzyme $Q_9$; purity 99.1%; reduced coenzyme $Q_{10}$/oxidized coenzyme $Q_{10}$ weight ratio 99.4/0.6) as obtained in the same manner as in Example 1 were dissolved in 140 g of acetonitrile at 45° C., and the solution was cooled to 2° C. while stirring (power required for stirring: 0.3 kW/$m^3$) to give a white slurry. All the above operations were carried out in a nitrogen atmosphere. The slurry obtained was filtered under reduced pressure, and the wet crystals were washed in sequence with cold acetonitrile, cold water and cold acetonitrile (the cold solvents used for washing having a temperature of 2° C.). The wet crystals were dried under reduced pressure (20–40° C., 1–30 mmHg) to give 9.5 g of dry white crystals (containing 0.25% of reduced coenzyme $Q_9$, percentage of elimination: 14%) (isolated product yield: 95 mole percent). The reduced coenzyme $Q_{10}$/oxidized coenzyme $Q_{10}$ weight ratio of the crystals obtained was 99.4/0.6, and the purity of the reduced coenzyme $Q_{10}$ was 99.1%.

EXAMPLE 12

Ten grams of crystals of reduced coenzyme $Q_{10}$ (containing 0.29% of reduced coenzyme $Q_9$; purity 98.8%; reduced coenzyme $Q_{10}$/oxidized coenzyme $Q_{10}$ weight ratio: 99.1/0.9) as obtained in the same manner as in Example 1 were dissolved in 100 g of heptane at 25° C., and the solution was cooled to 2° C. while stirring (power required for stirring: 0.3 kW/$m^3$) to give a white slurry. All the above operations were carried out in the air. The slurry obtained was filtered under reduced pressure, and the wet crystals were washed in sequence with cold heptane, cold ethanol, cold water, cold ethanol and cold heptane (the cold solvents used for washing having a temperature of 2° C.). The wet crystals were dried under reduced pressure (20–40° C., 1–30 mmHg) to give 9.3 g of dry white crystals (containing 0.20% of reduced coenzyme $Q_9$, percentage of elimination: 31%) (isolated product yield: 93 mole percent). The reduced coenzyme $Q_{10}$/oxidized coenzyme $Q_{10}$ weight ratio of the crystals obtained was 99.0/1.0, and the purity of the reduced coenzyme $Q_{10}$ was 98.8%.

COMPARATIVE EXAMPLE 3

Ten grams of the crystals of reduced coenzyme $Q_{10}$ as obtained in Example 1 were dissolved in 70 g of N-methylpyrrolidone at 25° C. Furthermore, 10 g of water was added, and the solution was cooled to 2° C. while stirring (power required for stirring: 0.3 kW/$m^3$) to give a pale-yellow slurry. All the above operations were carried out in the air. The slurry obtained was filtered under reduced pressure, and the wet crystals were washed in sequence with cold ethanol, cold water and cold ethanol (the cold solvents used for washing having a temperature of 2° C.). The wet crystals were dried under reduced pressure (20–40° C., 1–30 mmHg) to give 9.6 g of pale-yellow dry crystals (isolated product yield: 96 mole percent). The crystals obtained had a pale-yellow color, the reduced coenzyme $Q_{10}$/oxidized coenzyme $Q_{10}$ weight ratio was 88.6/11.4, and the purity of the reduced coenzyme $Q_{10}$ was 88.3%.

EXAMPLE 13

Oxidized coenzyme $Q_{10}$ (100 g) was dissolved in 1000 g of hexane at 25° C. While stirring (power required for stirring: 0.3 kW/$m^3$), an aqueous solution prepared by dissolving 40 g of sodium dithionite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the hexane phase was washed 6 times with 1000 g of a deaerated saturated aqueous sodium chloride solution. All the above operations were carried out in a nitrogen atmosphere. The reduced coenzyme $Q_{10}$/oxidized coenzyme $Q_{10}$ weight ratio in this hexane solution was 99.2/0.8.

EXAMPLE 14

Oxidized coenzyme $Q_{10}$ (100 g; purity 99.4%), 60 g of L-ascorbic acid and 30 g of sodium hydrogencarbonate were added to 1000 g of acetonitrile, and the reduction reaction was carried out with stirring at 55° C. After the lapse of 40 hours, 1000 g of heptane and 1000 g of deaerated water were added to the reaction mixture, and the resulting mixture was cooled to 25° C. The aqueous phase was removed from the reaction mixture, and the heptane phase was washed 6 times with 1000 g of a deaerated saturated aqueous sodium chloride solution. This heptane phase was cooled to 2° C. while stirring (power required for stirring: 0.3 kW/$m^3$) to give a white slurry. All the above operations were carried out in a nitrogen atmosphere. The slurry obtained was filtered under reduced pressure, and the wet crystals were washed in sequence with cold heptane, cold ethanol, cold water, cold ethanol and cold heptane (the cold solvents used for washing having a temperature of 2° C.). The wet crystals were further dried under reduced pressure (20–40° C., 1–30 mmHg) to give 95 g of dry white crystals (isolated product yield: 95 mole percent). The reduced coenzyme $Q_{10}$/oxidized coenzyme $Q_{10}$ weight ratio of the crystals obtained was 99.5/0.5, and the purity of the reduced coenzyme $Q_{10}$ was 99.0%.

COMPARATIVE EXAMPLE 4

The reduction reaction was carried out in the same manner as in Example 13 except that all the operations were carried out in the air. The reduced coenzyme $Q_{10}$/oxidized coenzyme $Q_{10}$ weight ratio in the hexane solution obtained was 45.3/54.7.

INDUSTRIAL APPLICABILITY

The invention, which has the constitution described above, is a method suited for commercial scale production and can give high-quality reduced coenzyme $Q_{10}$ in a convenient and efficient manner.

The invention claimed is:

1. A method of crystallizing reduced coenzyme $Q_{10}$, which comprises crystallizing the reduced coenzyme $Q_{10}$ using, as a solvent, at least one species selected from the group consisting of hydrocarbons, fatty acid esters, ethers and nitriles.

2. The method according to claim 1, wherein an aliphatic hydrocarbon is used as the solvent.

3. The method according to claim 2, wherein the aliphatic hydrocarbon is an acyclic aliphatic hydrocarbon.

4. The method according to claim 2, wherein the aliphatic hydrocarbon is at least one species selected from among pentanes, hexanes, heptanes and octanes.

5. The method according to claim 1, wherein an impurity is eliminated into the mother liquor.

6. The method according to claim 5, wherein the impurity to be eliminated is at least one species selected from among reduced coenzyme $Q_9$, reduced coenzyme $Q_8$ and reduced coenzyme $Q_7$.

7. The method according to claim 1, wherein the crystallization of reduced coenzyme $Q_{10}$ is carried out in the manner of crystallization by cooling or a combination of crystallization by cooling with another method of crystallization.

8. The method according to claim 7, wherein the cooling temperature in the step of crystallization is not higher than 20° C.

9. The method according to claim 1, wherein the crystallization concentration as expressed in terms of the weight of reduced coenzyme $Q_{10}$ based on the weight of the crystallization solvent at the time of completion of crystallization is not higher than 15 w/w %.

10. The method according to claim 1, wherein the crystallization is carried out under forced flowing caused by a power required for stirring per unit volume of not weaker than 0.01 $kW/m^3$.

11. The method according to claim 1, wherein a seed crystal is added in carrying out the crystallization.

12. The method according to claim 1, wherein the crystallization is carried out in a deoxygenated atmosphere.

13. A reduced coenzyme $Q_{10}$ crystal with a reduced coenzyme $Q_{10}$/oxidized coenzyme $Q_{10}$ weight ratio of not lower than 96/4.

14. A method of producing reduced coenzyme $Q_{10}$ which comprises using at least one species selected from among hydrocarbons exclusive of hexane, fatty acid esters and nitriles as a solvent in synthesizing reduced coenzyme $Q_{10}$ by reduction of oxidized coenzyme $Q_{10}$ and thereby protecting reduced coenzyme $Q_{10}$ from oxidation.

15. The method according to claim 14, wherein at least one species selected from among fatty acid esters and nitriles is used as the solvent.

16. The method according to claim 14, wherein the reduction is carried out in a deoxygenated atmosphere.

17. A method for preparing reduced coenzyme $Q_{10}$ which comprises using a hydrocarbon and/or an ether as a solvent in a deoxygenated atmosphere in synthesizing reduced coenzyme $Q_{10}$ by reduction of oxidized coenzyme $Q_{10}$ and thereby protecting reduced coenzyme $Q_{10}$ from oxidation.

18. The method according to claim 1, wherein the reduced coenzyme $Q_{10}$ to be subjected to the crystallization is a product obtainable by the method according to claim 14 or 17.

19. The method according to claim 1, wherein the crystallization of reduced coenzyme $Q_{10}$ is carried out from a reduction reaction mixture obtainable by the method according to claim 14 or 17, or a solution obtainable by separating an organic phase containing reduced coenzyme $Q_{10}$ and, if necessary, washing the organic phase.

20. The method according to claim 17, wherein a hydrocarbon is used as the solvent.

21. The method according to claim 20, wherein one of heptanes is used as the solvent.

22. The method according to claim 17, wherein an ether is used as the solvent.

23. The method according to claim 14 or 17, wherein a metal hydride compound, iron or zinc is used as the reducing agent.

24. The method according to claim 14 or 17, wherein the reduction is carried out in the presence of water using dithionous acid or a salt thereof as the reducing agent.

25. The method according to claim 24, wherein the reduction is carried out at pH 3 to 7.

26. The method according to claim 24, wherein the amount of dithionous acid or a salt thereof to be used equals to or is smaller than the amount of oxidized coenzyme $Q_{10}$ on the weight basis.

27. The method according to claim 14 or 17, wherein ascorbic acid or a related compound thereof is used as the reducing agent.

28. The method according to claim 27, wherein at least one highly water-miscible species selected from among ethers and nitriles is used as the solvent.

29. The method according to claim 27, wherein the amount of the ascorbic acid or a related compound thereof as used is not smaller than 1 mole per mole of oxidized coenzyme $Q_{10}$.

30. The method according to claim 27, wherein the reduction is carried out in the presence of a basic substance or a hydrogensulfite salt.

31. The method according to claim 14 or 17, wherein, after the reduction reaction, the organic phase containing the product reduced coenzyme $Q_{10}$ is recovered and washed with water.

* * * * *